United States Patent
Pan

(10) Patent No.: US 9,158,997 B2
(45) Date of Patent: Oct. 13, 2015

(54) METHOD FOR DISPLAYING MAMMOGRAPHY IMAGES

(71) Applicant: EBM Technologies Incorporated, Taipei (TW)

(72) Inventor: William Pan, Taipei (TW)

(73) Assignee: EBM TECHNOLOGIES INCORPORATED, Taipei (TW)

( * ) Notice: Subject to any disclaimer, the term of this patent is extended or adjusted under 35 U.S.C. 154(b) by 50 days.

(21) Appl. No.: 14/226,178

(22) Filed: Mar. 26, 2014

(65) Prior Publication Data

US 2015/0139523 A1   May 21, 2015

(51) Int. Cl.
  *G06K 9/00* (2006.01)
  *G06K 9/62* (2006.01)
  *G06F 19/00* (2011.01)

(52) U.S. Cl.
  CPC .............. *G06K 9/6267* (2013.01); *G06F 19/30* (2013.01); *G06K 9/6202* (2013.01)

(58) Field of Classification Search
  CPC ....................................... G06K 9/62
  USPC ......................................................... 382/132
  See application file for complete search history.

(56) References Cited

U.S. PATENT DOCUMENTS

| 2003/0031353 A1* | 2/2003 | Baertsch et al. | 382/132 |
| 2010/0080427 A1* | 4/2010 | Yeluri et al. | 382/128 |
| 2011/0206261 A1* | 8/2011 | Huo et al. | 382/132 |

* cited by examiner

*Primary Examiner* — Gregory F Cunningham
(74) *Attorney, Agent, or Firm* — Muncy, Geissler, Olds & Lowe, P.C.

(57) ABSTRACT

In a method for displaying mammography images, an identification of the mammography images is first inputted via a user interface of a computer system. A host is employed to receive the identification for activating the mammography images and reading a header of the mammography images. The host reads a plurality of displaying rules previously configured for comparing with the header of the mammography images. The host then automatically selects one of the plurality of displaying rules that is best conformed to the header of the mammography images. The host automatically classifies the mammography images according to the selected one displaying rule. Finally, a monitor displays the classified mammography images.

10 Claims, 8 Drawing Sheets

METHOD FOR DISPLAYING MAMMOGRAPHY IMAGES

BACKGROUND OF THE INVENTION

1. Field of the Invention

The present invention relates to a method for displaying mammography images.

2. Description of Related Art

Mammography is an essential screening tool to diagnose the early breast cancer. The prior mammograms are negative-film images obtained by a mammography machine with an ionizing radiation passing through breasts. In practice, one examination may take mammography on the same breast at different directions in order to obtain various sections of mammography images. Next, a doctor can manually suspend a plurality of mammograms on a plurality of light boxes in a consulting room to inspect and compare one by one for any abnormal findings. Sometimes, the mammograms in a previous examination or other mammograms are inspected for reference. Otherwise, for convenient comparison, an order and direction of suspended mammograms are adaptively adjusted. When more parallel mammograms are required, it is not satisfactory because the number of light boxes or the place is limited. Such manually suspending way and demand of the light boxes are inconvenient, time-wasting, expensive, and difficult to increase the diagnostic efficiency.

Accordingly, a special suspending method for the mammograms is provided to meet with the habitual behaviors of people and individual in use, the medical environments, and the operation procedures. However, the effectiveness is limited due to the manually suspending way, even the special suspending method is provided.

Therefore, it is desired to provide a method for displaying mammography images for improving the above displaying method without changing the old suspending habit, so that the practice and completeness are satisfied.

SUMMARY OF THE INVENTION

The object of the present invention is to provide a method for displaying mammography images, which is implemented on a computer system having a host, a user interface connected to the host, and a monitor connected to the host. The method includes the steps of: (A) inputting an identification of the mammography images via the user interface; (B) using the host to receive the identification for activating the mammography images and reading a header of the mammography images; (C) using the host to read a plurality of displaying rules previously configured for comparing with the header of the mammography images; (D) using the host to automatically select one of the plurality of displaying rules that is best conformed to the header of the mammography images; (E) automatically classifying the mammography images by the host according to the selected one displaying rule, and adaptively changing settings of the selected one of the displaying rules via the user interface; and (F) displaying classified mammography images via the monitor.

Thus, the method in the invention can display special regions or types of the mammography images by inputting the identification of the mammography images via the user interface and using the classification, without manually classifying and suspending as cited in the prior art.

In addition, the host is based on the header of the mammography images to classify the image attributes including birthday, gender, examining date, examining description, examining amount, examining region, image type, image description, and image amount.

Further, the examining date includes current and previous examining dates.

Further, the examining region includes left and right breast fronts and left and right breast laterals.

Further, the image type includes cranial-caudal (CC) view and medial-lateral oblique (MLO) view types.

Further, the displaying rules are obtained by using the user interface to select multiple displaying stages. The displaying stages include image arrangement, location, direction, rotation, alignment, and tool settings.

Further, the image arrangement setting configures the mammography images into a matrix arrangement via the user interface.

Further, the image location setting exchanges the relative positions of the mammography images via the user interface.

Further, the image tool setting includes masks and magnifiers.

Finally, the computer system further includes a server. The host downloads the mammography images corresponding to the identification from the server.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
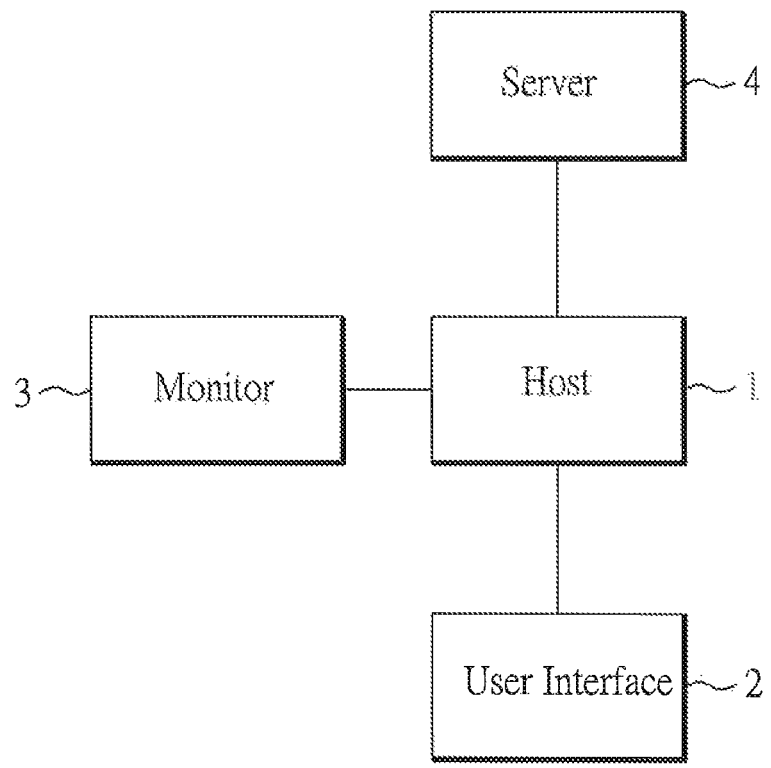
FIG. 1 is a configuration diagram of a system implemented with a method for displaying mammography images according to the invention.
Figure 2:
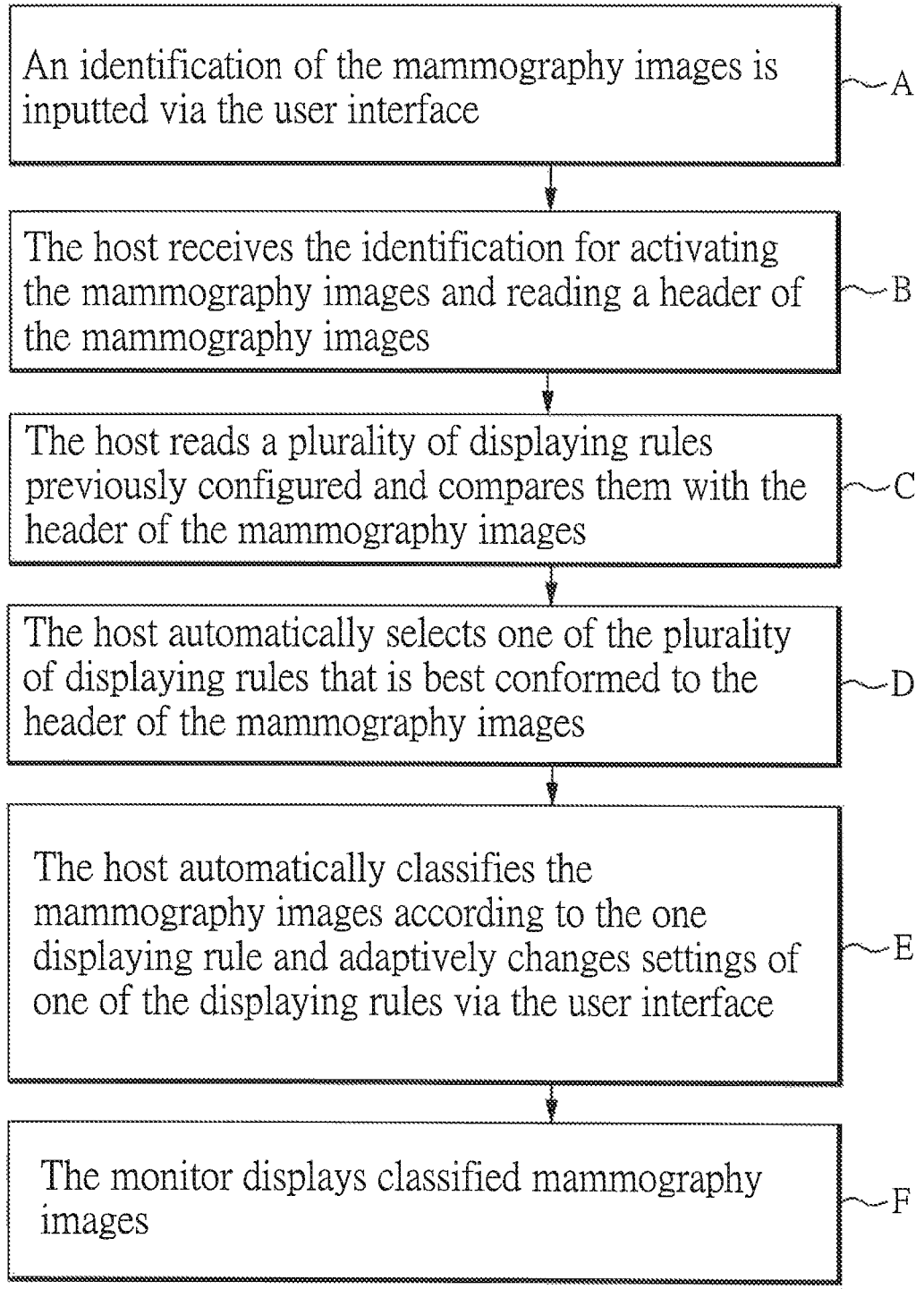
FIG. 2 is a flowchart of a method for displaying mammography images according to the invention.

FIG. 1 is a configuration diagram of a system implemented with a method for displaying mammography images according to the invention. FIG. 2 is a flowchart of the method for displaying mammography images according to the invention. As shown in FIGS. 1 and 2, the method is applied on a computer system, which includes a host 1, a user interface 2 connected to the host 1, a monitor 3 connected to the host 1, and a server 4. The server 4 stores the mammography images of all patients, and the mammography images of each patient have a unique identification. The host 1 downloads the mammography images of the patient from the server 4 for inspection. The method includes the steps of: (A) inputting an identification of the mammography images via the user interface 2, (B) using the host 1 to receive the identification for activating the mammography images and reading a header of the mammography images, (C) using the host 1 to read a plurality of displaying rules previously configured for comparing with the header of the mammography images, (D) using the host to automatically select one of the plurality of displaying rules that is best conformed to the header of the mammography images, (E) automatically classifying the mammography images by the host 1 according to the selected one displaying rule, and (F) displaying classified mammography images via the monitor 3. In step (D), the host 1 can allow a user to configure the displaying rules required for displaying the mammography images. Each displaying rule is obtained by using the user interface 2 to select multiple displaying stages as required. Namely, the displaying rules are comprised of different sequences of the displaying stages. The displaying stages include image arrangement, location, direction, rotation, alignment, and tool settings. The image arrangement setting can configure the mammography images into a matrix arrangement via the user interface 2. For example, a 4×2, 2×2, 2×1, or other matrix is arranged. The image location setting can exchange the relative positions of the mammography images via the user interface 2. The image direction setting can exchange the direction of the mammography images via the user interface 2. The image rotation setting can rotate the mammography images (such as a 180 degree rotation) via the user interface 2. The image alignment setting can automatically classify the mammography images based on image attributes and align at left or right. The image tool setting can include masks and magnifiers. The host 1 is based on the header of the mammography images to classify the image attributes including birthday, gender, examining date, examining description, examining amount, examining region, image type, image description, and image amount. The examining date attribute includes current and previous examining dates. The examining region attribute includes left and right breast fronts and left and right breast laterals. The image type attribute includes cranial-caudal (CC) view and medial-lateral oblique (MLO) view types. In step (E), the settings of one of the displaying rules can be adaptively changed via the user interface 2. Namely, when the host 1 classifies the mammography images, the user can change the displaying stages of the selected one displaying rule into a new displaying rule via the user interface 2 anytime, so that the host 1 can apply the new displaying rule subsequently.

Figure 3:
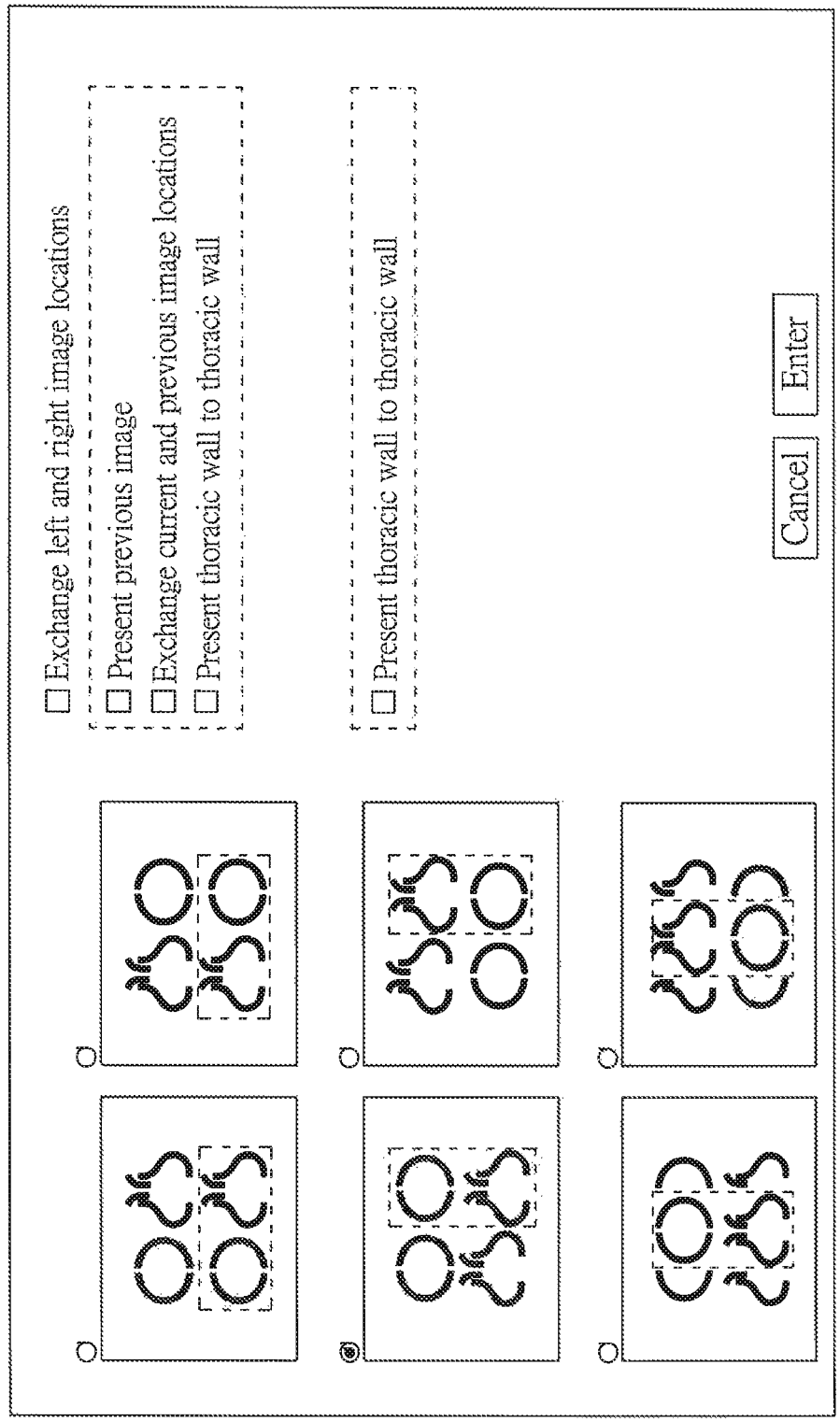
FIG. 3 is a schematic diagram of a user interface applied to mammography images according to the invention.
Figures 4, 5, 6:
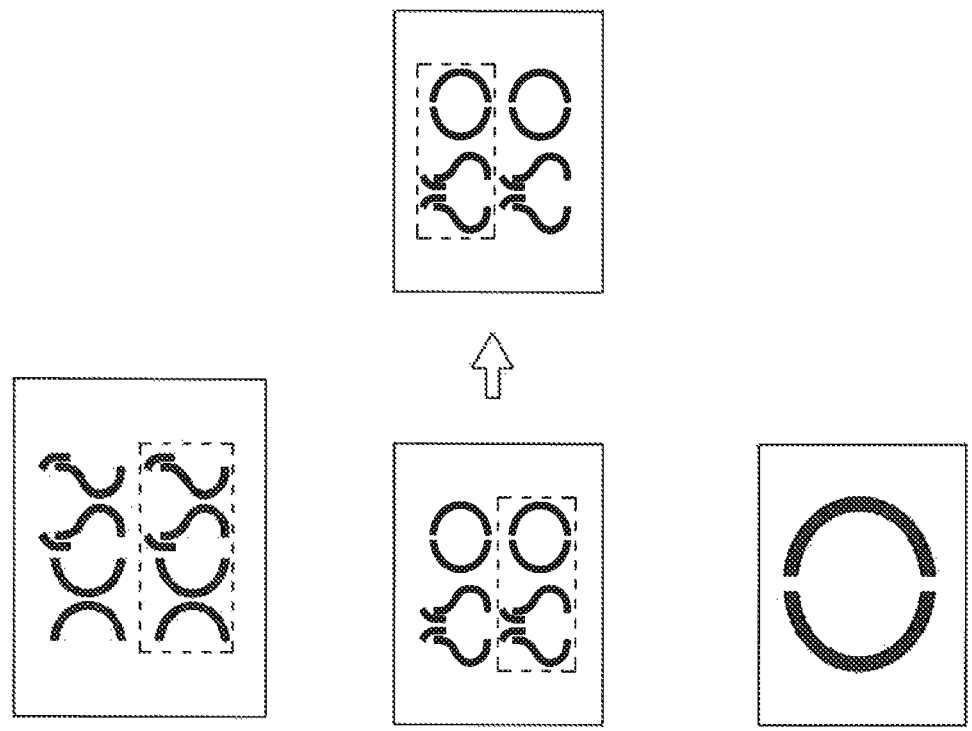
FIG. 4 is a schematic diagram of exchanging left and right mammography images according to the invention.
FIG. 5 is a schematic diagram of exchanging current and previous mammography images according to the invention.
FIG. 6 is a schematic diagram of presenting thoracic wall to thoracic wall mammography images according to the invention.

FIG. 3 is a schematic diagram of a user interface applied to mammography images according to the invention, which illustrates all mammography image settings in the displaying stages. Mammography typically takes four images including left and right breast fronts and left and right breast laterals in each examination. In the image arrangement settings, the six matrices at the left side of FIG. 3 are used to indicate the currently examining images inside a dot line box and the previously examining images outside the dot box. After the arrangement is selected, the other image settings can be configured. For example, the image location and direction settings, e.g., the options of exchanging left and right image locations, presenting previous images, exchanging current and previous image locations, or presenting thoracic wall to thoracic wall at the right side of FIG. 3, are configured, where the settings inside the dot line box correspond to the mammography images at the left side only, and the option of exchanging left and right image locations exchanges the images in the six arrangements at the left side only. FIG. 4 is a schematic diagram of exchanging left and right mammography images according to the invention, which indicates that the left and right mammography images at the leftmost upper side are exchanged, and the left and right mammography images in the other five ones are exchanged when the exchanging left and right image locations setting is selected. FIG. 5 is a schematic diagram of exchanging current and previous examining images according to the invention, which exchanges the current and previous examining images at the upper and lower sides inside the dot line box. FIG. 6 is a schematic diagram of presenting thoracic wall to thoracic wall mammography images according to the invention, which presents the current and previous examining images in different directions.

Figure 7:
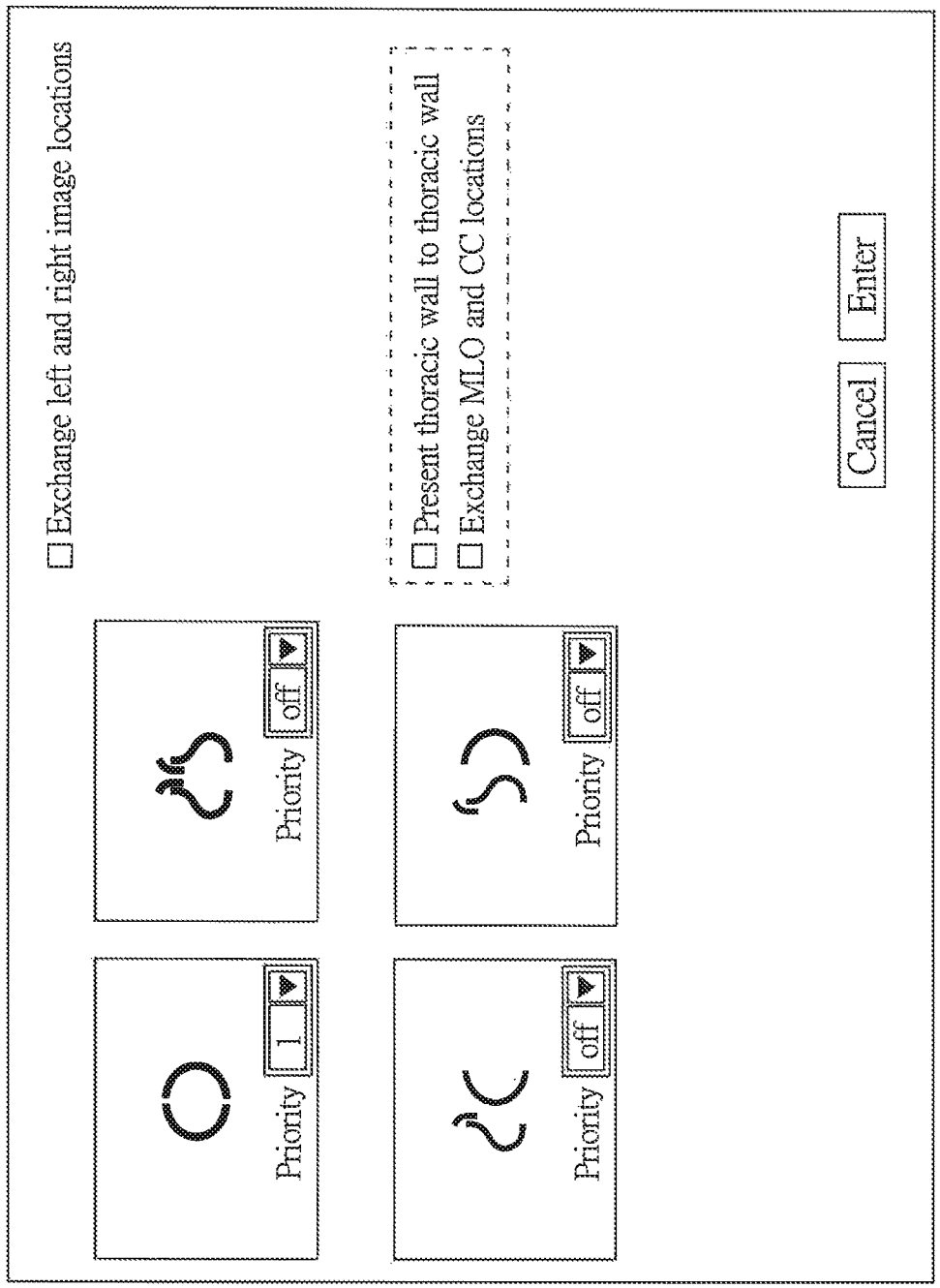
FIG. 7 is a schematic diagram of another user interface applied to mammography images according to the invention.
Figure 8:
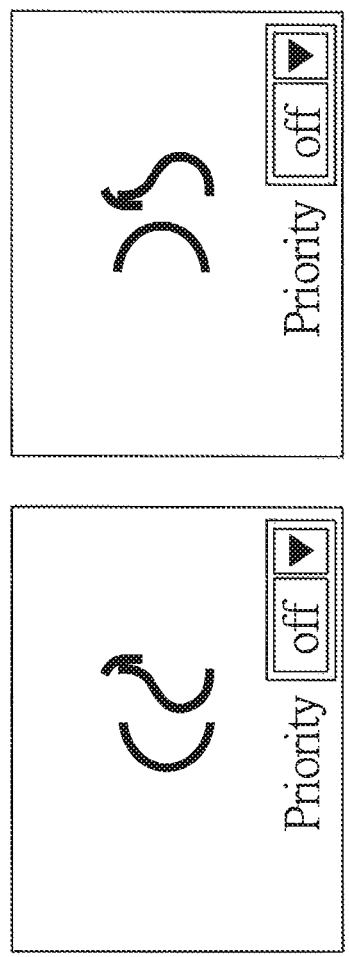
FIG. 8 is a schematic diagram of exchanging cranial-caudal (CC) view and medial-lateral oblique (MLO) view types of mammography images according to the invention.

FIG. 7 is a schematic diagram of another user interface applied to mammography images according to the invention, which is a user interface for the mammography image presenting priority. A priority indicates a mammography image presenting sequence. When the priority is set to one, it indicates that the first presentation, and so on. When the priority is set to off; it indicates that the settings are not applied. FIG. 8 is a schematic diagram of exchanging cranial-caudal (CC) view and medial-lateral oblique (MLO) view types of mammography images according to the invention, which indicates that the mammography images are exchanged when the exchanging MLO and CC locations at the right side of FIG. 7 is selected.

Figure 9:
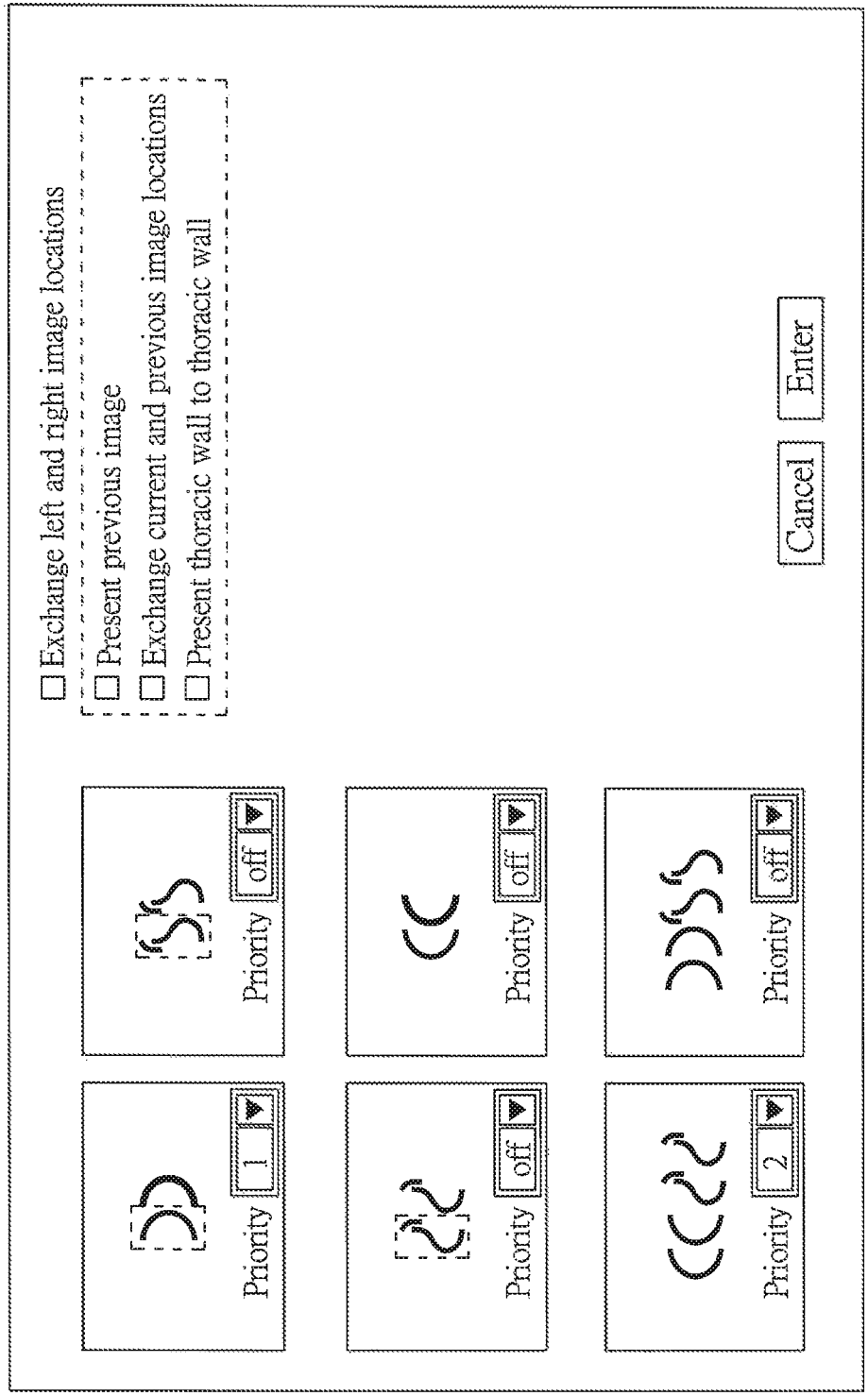
FIG. 9 is a schematic diagram of a further user interface applied to mammography images according to the invention.
Figure 10:
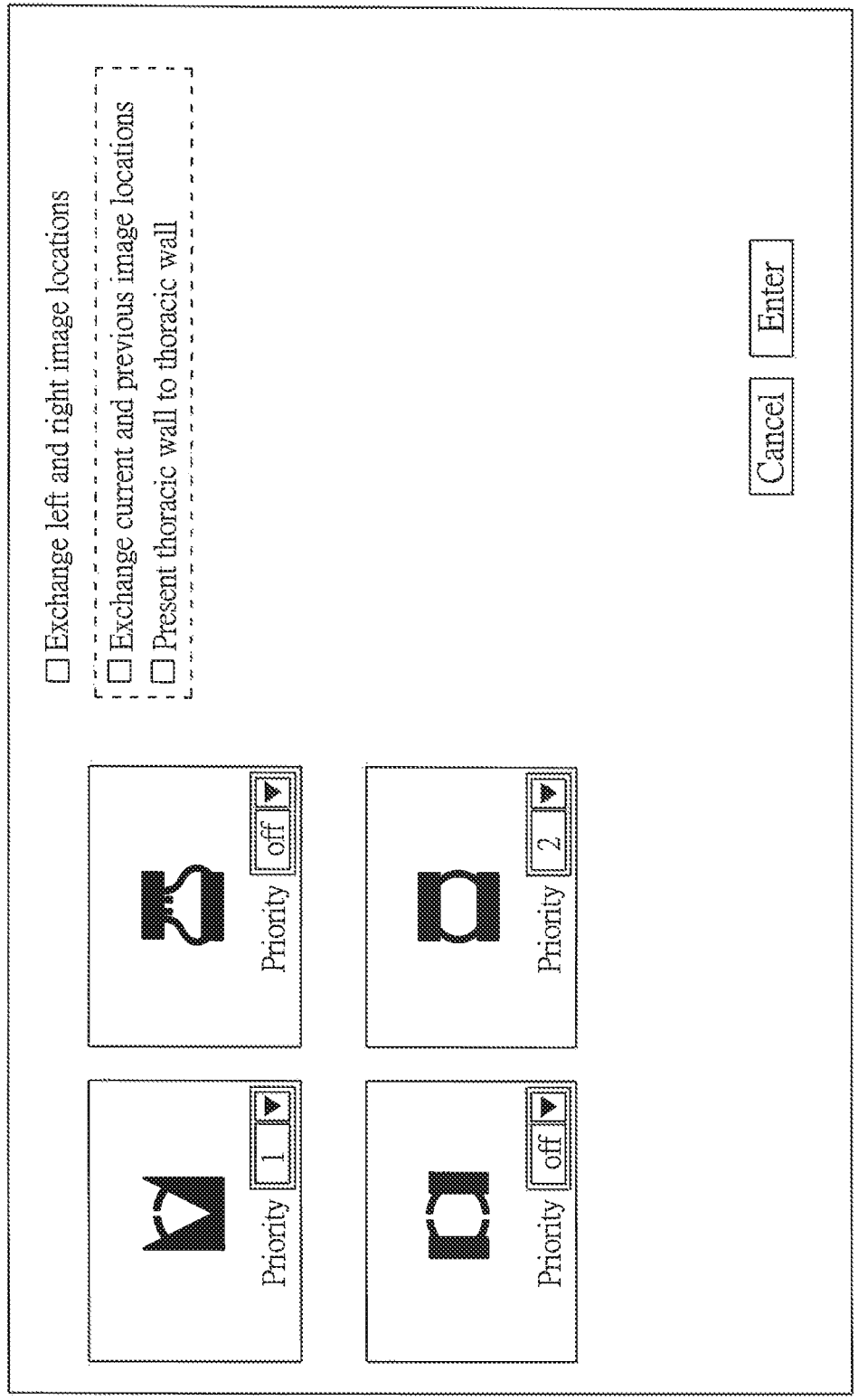
FIG. 10 is a schematic diagram of further another user interface applied to mammography images according to the invention.

FIG. 9 is a schematic diagram of a further user interface applied to mammography images according to the invention, which illustrates the display stage settings when different images are compared. FIG. 10 is a schematic diagram of further another user interface applied to mammography images according to the invention, which illustrates the display stage settings when a mask is used.

When the settings for the displaying stages are assigned or configured, the host 1 records the settings at this time to form a displaying rule. For a next mammography image inspection, the host 1 reads a plurality of displaying rules previously configured and compares them with the header of the mammography images, such that the host 1 can automatically select one of the plurality of displaying rules that is best conformed to the header of the mammography images, thereby applying the one displaying rule to the mammography images for displaying on the monitors. Therefore, the mammography images are displayed at the preferred performance, and the mammography becomes more convenient and accurate.

Although the present invention has been explained in relation to its preferred embodiment, it is to be understood that many other possible modifications and variations can-be made without departing from the spirit and scope of the invention as hereinafter claimed.

What is claimed is:
1. A method for displaying mammography images, implemented on a computer system having a host, a user interface connected to the host, and a monitor connected to the host, the method comprising the steps of:
  (A) inputting an identification of the mammography images via the user interface;
  (B) using the host to receive the identification for activating the mammography images and reading a header of the mammography images;
  (C) using the host to read a plurality of displaying rules previously configured for comparing with the header of the mammography images;

(D) using the host to automatically select one of the plurality of displaying rules that is best conformed to the header of the mammography images;
(E) automatically classifying the mammography images by the host according to the selected one displaying rule, and adaptively changing settings of the selected one of the displaying rules via the user interface; and
(F) using the monitor to display classified mammography images.

2. The method as claimed in claim 1, wherein the host is based on the header of the mammography images to classify the image attributes including birthday, gender, examining date, examining description, examining amount, examining region, image type, image description, and image amount.

3. The method as claimed in claim 2, wherein the examining date comprises current and previous examining dates.

4. The method as claimed in claim 3, wherein the examining region comprises left and right breast fronts and left and right breast laterals.

5. The method as claimed in claim 4, wherein the image type comprises cranial-caudal (CC) view and medial-lateral oblique (MLO) view types.

6. The method as claimed in claim 5, wherein the displaying rules are obtained by using the user interface to select multiple displaying stages including image arrangement, location, direction, rotation, alignment, and tool settings.

7. The method as claimed in claim 6, wherein the image arrangement setting configures the mammography images into a matrix arrangement via the user interface.

8. The method as claimed in claim 7, wherein the image location setting exchanges relative positions of the mammography images via the user interface.

9. The method as claimed in claim 8, wherein the image tool setting comprises masks and magnifiers.

10. The method as claimed in claim 1, wherein the computer system further comprises a server for allowing the host to download the mammography images corresponding to the identification from the server.

* * * * *